United States Patent
Park et al.

(10) Patent No.: US 10,355,455 B2
(45) Date of Patent: Jul. 16, 2019

(54) PHOTONIC CRYSTAL LASER AND STRAIN MEASURING DEVICE

(71) Applicant: KOREA UNIVERSITY RESEARCH AND BUSINESS FOUNDATION, Seoul (KR)

(72) Inventors: Hong-Gyu Park, Seoul (KR); Jae-Hyuck Choi, Seoul (KR); Soon-Hong Kwon, Gyeonggi-do (KR); Kyoung-Ho Kim, Chungcheongnam-do (KR); You-Sin No, Seoul (KR); Jaepil So, Seoul (KR); JungMin Lee, Seoul (KR); Minsoo Hwang, Seoul (KR)

(73) Assignee: KOREA UNIVERSITY RESEARCH AND BUSINESS FOUNDATION, Seoul (KR)

( * ) Notice: Subject to any disclaimer, the term of this patent is extended or adjusted under 35 U.S.C. 154(b) by 56 days.

(21) Appl. No.: 15/366,350

(22) Filed: Dec. 1, 2016

(65) Prior Publication Data

US 2018/0041011 A1  Feb. 8, 2018

(30) Foreign Application Priority Data

Aug. 3, 2016 (KR) .................. 10-2016-0098732

(51) Int. Cl.
*H01S 5/343* (2006.01)
*H01S 5/02* (2006.01)
(Continued)

(52) U.S. Cl.
CPC ............ *H01S 5/34313* (2013.01); *G01L 1/24* (2013.01); *G01N 21/27* (2013.01); *G01N 21/77* (2013.01); *H01S 5/0071* (2013.01); *H01S 5/0206* (2013.01); *H01S 5/028* (2013.01); *H01S 5/0217* (2013.01); *H01S 5/041* (2013.01); *H01S 5/105* (2013.01); *H01S 5/3434* (2013.01); *H01S 5/42* (2013.01); *G01N 2021/7756* (2013.01);
(Continued)

(58) Field of Classification Search
CPC .. H01S 5/34313; H01S 5/0071; H01S 5/0206; H01S 5/0217; H01S 5/028; H01S 5/105; G01L 1/24; G01N 21/27; G01N 21/77
USPC ................................................ 422/82.05
See application file for complete search history.

(56) References Cited

U.S. PATENT DOCUMENTS 7,310,463 B2 * 12/2007 Shimotsuma .......... B82Y 20/00
                                                            385/11
7,630,589 B2   12/2009 Kilic et al.
(Continued)

OTHER PUBLICATIONS

Taylor, "Design of Photonic Crystal Surface Emitting Lasers and the Realisation of Coherently Coupled Arrays," Ph.D. Thesis, University of Sheffield, pp. i-ix, 1-165, dated Jan. 2015.
(Continued)

*Primary Examiner* — Jill A Warden
*Assistant Examiner* — Jacqueline Brazin
(74) *Attorney, Agent, or Firm* — Jenkins, Wilson, Taylor & Hunt, P.A.

(57) ABSTRACT

A photonic crystal laser and a strain measuring device are provided. The photonic crystal laser includes a disk-shaped photonic crystal structure two-dimensionally disposed in a matrix on a disposition plane and a flexible substrate disposed to support the photonic crystal structure and to cover at least a side surface of the photonic crystal structure.

8 Claims, 12 Drawing Sheets

(51) Int. Cl.
| | |
|---|---|
| *G01N 21/77* | (2006.01) |
| *H01S 5/00* | (2006.01) |
| *G01L 1/24* | (2006.01) |
| *G01N 21/27* | (2006.01) |
| *H01S 5/10* | (2006.01) |
| *H01S 5/028* | (2006.01) |
| *H01S 5/04* | (2006.01) |
| *H01S 5/42* | (2006.01) |
| *H01S 5/187* | (2006.01) |

(52) U.S. Cl.
CPC ........... *G01N 2021/7769* (2013.01); *G01N 2201/0612* (2013.01); *G01N 2201/0697* (2013.01); *H01S 5/0028* (2013.01); *H01S 5/187* (2013.01); *H01S 5/34326* (2013.01)

(56) References Cited

U.S. PATENT DOCUMENTS

| | | | |
|---|---|---|---|
| 7,760,364 B1* | 7/2010 | Zhuang | B82Y 20/00 356/237.1 |
| 8,670,471 B2* | 3/2014 | Kim | B82Y 20/00 372/21 |
| 9,130,347 B2 | 9/2015 | Scofield et al. | |
| 2007/0097680 A1* | 5/2007 | Cao | B82Y 20/00 362/231 |
| 2008/0226217 A1 | 9/2008 | Kilic et al. | |
| 2010/0288341 A1* | 11/2010 | Kim | B82Y 20/00 136/252 |
| 2014/0064310 A1* | 3/2014 | Chua | H01S 5/18 372/45.01 |
| 2014/0286367 A1* | 9/2014 | Scofield | H01S 5/1042 372/43.01 |

OTHER PUBLICATIONS

Korean Office Action for Korean Application No. KR 10-2016-0098732 dated Sep. 25, 2017.

\* cited by examiner

PHOTONIC CRYSTAL LASER AND STRAIN MEASURING DEVICE

CROSS-REFERENCE TO RELATED APPLICATION

This U.S. non-provisional application claims priority under 35 U.S.C. § 119 to Korea Patent Application No. 10-2016-0098732 filed on Aug. 3, 2016, the entirety of which is hereby incorporated by reference herein.

TECHNICAL FIELD

The present disclosure relates generally to a photonic crystal laser for varying a wavelength depending on mechanical change and, more particularly, to a strain sensor for detecting a transformation using a photonic crystal laser.

BACKGROUND

A photonic crystal is a periodic optical nanostructure having an effect on photons. A user using the photonic crystal externally receives a pump beam to generate a laser beam having a longer wavelength than the pump beam. When an InGaAsP quantum well structure is used as a gain medium, the photonic crystal laser generates a laser beam at a wavelength of about 1550 nm.

An existing strain gauge has been manufactured in such a way to measure resistance variation. An existing strain gauge for measuring resistance variation is limited in measuring range and resolution. Accordingly, there is a need for a strain sensor with improved measuring range and resolution.

SUMMARY

Example embodiments of the present disclosure provide a wavelength-variable photonic crystal laser for varying a frequency depending on a transformation.

Example embodiments of the present disclosure provide a strain sensor for measuring a transformation caused by a tensile force and a compressive force as a frequency of light.

Example embodiments of the present disclosure provide a method for fabricating a novel high-resolution strain sensor using a high-grade photonic crystal laser characterized in high resolution.

A photonic crystal laser according to an example embodiment of the present disclosure includes: a disk-shaped photonic crystal structure two-dimensionally disposed in a matrix on a disposition plane; and a flexible substrate disposed to support the photonic crystal structure and to cover at least a side surface of the photonic crystal structure.

In an example embodiment, an arrangement period of the photonic crystal structure may be between 550 and 700 nm, and the photonic crystal structure may oscillate in a Γ-point band-edge mode.

In an example embodiment, a laser gain medium of the photonic crystal structure may be InGaAsP spontaneously emitted at an infrared area or AlGaAs spontaneously emitted around 650 nm.

In an example embodiment, the photonic crystal structure may include an InGaAsP lower cladding layer, a quantum well InGaAsP active layer, and an InGaAsP upper cladding layer that are sequentially stacked.

In an example embodiment, the flexible substrate may include polydimethylsiloxane (PDMS), polyimide or polyethylene terephthalate (PET).

In an example embodiment, the photonic crystal laser may further include pressure applying means for applying a strain to the flexible substrate.

A method for fabricating a photonic crystal layer according to an example embodiment of the present disclosure includes: forming an etch-stop layer on a substrate; forming a buffer layer on the etch-stop layer; forming a photonic crystal active layer on the buffer layer; coating a resist on the photonic crystal active layer and patterning the coated resist to form a resist mask; dry-etching the photonic crystal active layer and the buffer layer using the resist mask as an etch mask to form a two-dimensionally disposed photonic crystal structure; selectively wet-etching the buffer layer of the photonic crystal structure to form a thinned photonic crystal support; coating and curing a polymer on the substrate where the thinned photonic crystal support is formed; removing the substrate to provide the photonic crystal structure buried in the polymer; and removing the thinned photonic crystal support through wet etching.

In an example embodiment, the substrate may be InP, the etch-stop layer may be InGaAs, the buffer layer may be InP, and the photonic crystal active layer may include includes InGaAsP.

In an example embodiment, the polymer may include at least one of polydimethylsiloxane (PDMS), polyimide or polyethylene terephthalate (PET).

In an example embodiment, the dry etching may be chemically assisted ion beam etching performed by accelerating argon ions under a chlorine gas atmosphere.

A strain measuring device according to an example embodiment of the present disclosure includes: a photonic crystal laser buried in a flexible substrate; a pump beam source configured to provide a pump beam to the photonic crystal laser; a wavelength detector configured to detect a laser wavelength varying depending on an external pressure applied to the photonic crystal laser; and a processor configured to calculate the degree of transformation of the photonic crystal laser using the laser wavelength.

In an example embodiment, the photonic crystal laser may include: a disk-shaped photonic crystal structure two-dimensionally disposed in a matrix on a disposition plane; and a flexible substrate disposed to support the photonic crystal structure and to cover at least a side surface of the photonic crystal structure.

In an example embodiment, an arrangement period of the photonic crystal structure may be between 550 and 700 nm.

In an example embodiment, a laser gain medium of the photonic crystal structure may be InGaAsP spontaneously emitted at an infrared area or AlGaAs spontaneously emitted around 650 nm.

In an example embodiment, the optical crystal structure may include an InGaAsP lower cladding layer, a quantum well InGaAsP active layer, and an InGaAsP upper cladding layer that are sequentially stacked.

In an example embodiment, the strain measuring device may further include at least one of: a dichromatic mirror configured to receive the pump beam emitted from the pump beam source and transmit the received pump beam to the photonic crystal laser and configured to receive a laser beam emitted from the photonic crystal laser and transmit the received laser beam to a spectrometer; a parallel beam lens disposed between the pump beam source and the dichromatic mirror; and an object lens disposed between the dichromatic mirror and the photonic crystal laser to focus the pump beam onto the photonic crystal laser.

In an example embodiment, the strain measuring device may further include at least one of: an illumination light source configured to output an illumination light; a beam coupler disposed between the dichromatic mirror and the object lens to receive and provide the illumination light to the photonic crystal laser; a reflection mirror disposed between the dichromatic mirror and the spectrometer to change a beam path; a beam splitter disposed between the reflection mirror and the spectrometer to split a beam; and a camera configured to pick up an image using a beam split from the beam splitter.

In an example embodiment, the flexible substrate may include at least one of polydimethylsiloxane (PDMS), polyimide or polyethylene terephthalate (PET).

In an example embodiment, an output of the pump beam may be greater than or equal to 600 microwatts.

A pH sensor based on a photonic crystal laser according to an example embodiment of the present disclosure includes: a housing having a cavity formed therein and including an inlet channel and an outlet channel; a pH-sensitive hydrogel disposed inside the housing; and a photonic crystal laser disposed on one surface of the housing. The pH-sensitive hydrogel may provide a volume variation depending on a pH level of a liquid solution, and the photonic crystal laser may be transformed by the volume variation.

In an example embodiment, the photonic crystal laser may include: a disk-shaped photonic crystal structure two-dimensionally disposed in a matrix on a disposition plane; and a flexible substrate disposed to support the photonic crystal structure and to cover at least a side surface of the photonic crystal structure.

A pH measuring device according to an example embodiment of the present disclosure includes: a pH sensor based on a photonic crystal laser; a pump beam source configured to provide a pump beam to the photonic crystal laser; a wavelength detector configured to detect a laser wavelength varying depending on an external pressure applied to the photonic crystal laser; and a processor configured to calculate the transformation degree of the photonic crystal laser using the laser wavelength.

In an example embodiment, the pH sensor based on the photonic crystal laser may include: a housing having a cavity formed therein and including an inlet channel and an outlet channel; a pH-sensitive hydrogel disposed inside the housing; and a photonic crystal laser disposed on one surface of the housing. The pH-sensitive hydrogel may provide a volume variation depending on a pH level of a liquid solution, and the photonic crystal laser may be transformed by the volume variation.

BRIEF DESCRIPTION OF THE DRAWINGS

The present disclosure will become more apparent in view of the attached drawings and accompanying detailed description. The embodiments depicted therein are provided by way of example, not by way of limitation, wherein like reference numerals refer to the same or similar elements. The drawings are not necessarily to scale, emphasis instead being placed upon illustrating aspects of the present disclosure.

DETAILED DESCRIPTION

Figure 1:
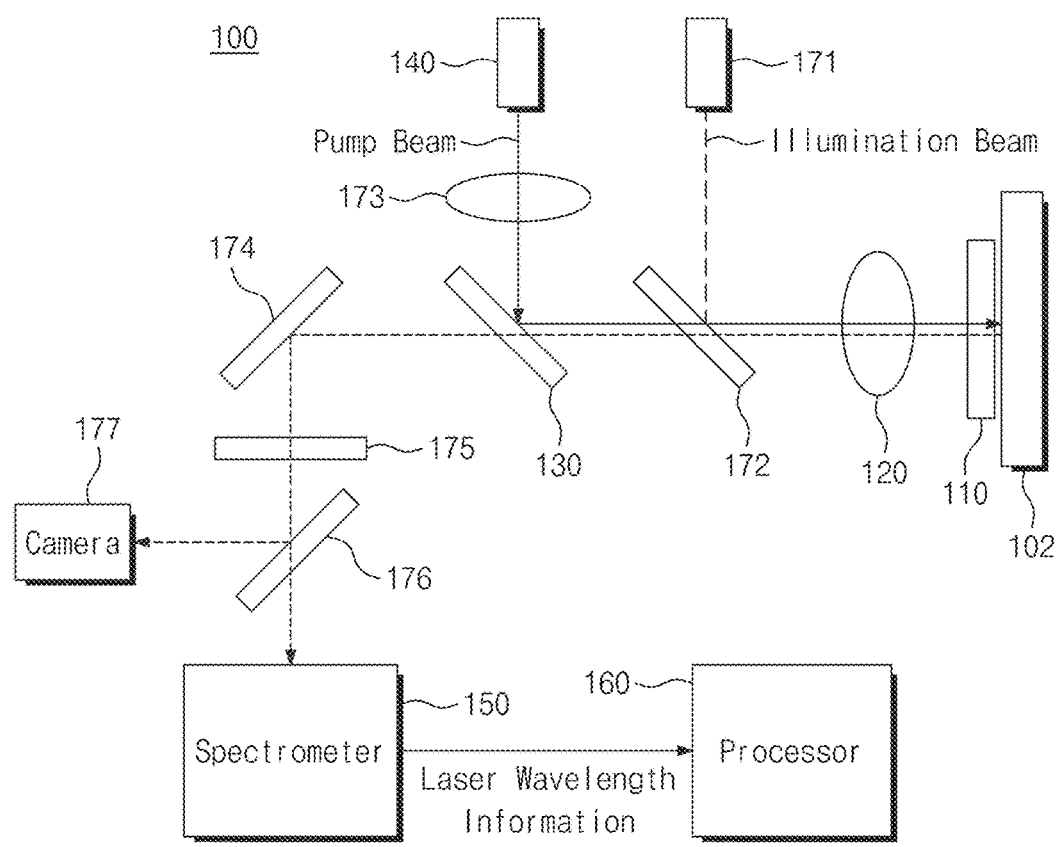
FIG. 1 is a conceptual diagram of a strain measuring device according to an example embodiment of the present disclosure.

According to an example embodiment of the present disclosure, a nanolaser is provided using a photonic crystal structure. The periodicity of the photonic crystal structure is around the wavelength of light. The photonic crystal structure is a structure in which two materials having different refractive indices are repeated. A photonic crystal nanolaser was fabricated by burying a photonic crystal structure having repeatedly arranged nail-like shapes in a flexible support material (or a flexible substrate). The nanolaser is a new type of photonic crystal laser whose wavelength varies when an external pressure is applied, e.g., a laser structure is stretched or compressed.

The laser wavelength of the photonic crystal laser is determined according to the lattice structure of a photonic crystal. A lattice period of the photonic crystal structure and the laser wavelength vary depending on an external pressure. Based on the principle, a pressure applied to the structure or change of the structure may be measured. In particular, since laser has a very narrow linewidth of wavelength, variation of the wavelength may be sensitively sensed. Therefore, utilization of the laser as a sensor is high.

Wavelength variation of a photonic crystal laser was experimentally measured according to a minute change in structure. A flexible photonic crystal laser exhibits a laser wavelength variation of about 26 nm during change from −10 percent to 12 percent. Considering that a linewidth of the laser wavelength is less than about 0.6 nm, the wavelength variation is very great. That is, since linewidth corresponding to gradation of a sensor is very narrow and the operation range is wide, the laser may operate as a high-sensitivity pressure sensor. In addition, a camera was allowed to confirm that a polarization and a shape of a laser mode varied depending on a direction in which the laser structure is transformed. This is a first test result which is capable of visually viewing whether there is a pressure and a direction in which the pressure is applied.

A novel method capable of measuring the acidity (pH) of a liquid using the pressure sensor is provided. If a hydrogel whose volume varies in reaction to the acidity of a liquid is attached to the pressure sensor, a chemical sensor which can optically sense acidity is implemented. When the liquid is injected, the volume of a pH-sensitive hydrogel varies and a pressure is applied to the pressure sensor. At this point, variation of a laser wavelength is measured, which the principle of the present disclosure. Acidity was successfully measured in three states including a dry state, a weak acid state (pH 2.5, acetic acid), and a neutral state (pH 7). It was checked that as the acidity varied, variation of the laser wavelength varied stably and reversibly.

Advantages and features of the present disclosure and methods of achieving them will be apparent from the following exemplary embodiments that will be described in more detail with reference to the accompanying drawings. It should be noted, however, that the present disclosure is not limited to the following exemplary embodiments, and may be implemented in various forms. Accordingly, the exemplary embodiments are provided only to disclose the present disclosure and let those skilled in the art know the category of the present disclosure.

In the specification, it will be understood that when an element is referred to as being "on" another layer or substrate, it can be directly on the other element, or intervening elements may also be present. In the drawings, thicknesses of elements are exaggerated for clarity of illustration.

Exemplary embodiments of the present disclosure will be described below with reference to cross-sectional views, which are exemplary drawings of the present disclosure. The exemplary drawings may be modified by manufacturing techniques and/or tolerances. Accordingly, the exemplary embodiments of the present disclosure are not limited to specific configurations shown in the drawings, and include modifications based on the method of manufacturing the semiconductor device. For example, an etched region shown at a right angle may be formed in a rounded shape or formed to have a predetermined curvature. Therefore, regions shown in the drawings have schematic characteristics. In addition, the shapes of the regions shown in the drawings exemplify specific shapes of regions in an element, and do not limit the present disclosure. Though terms like a first, a second, and a third are used to describe various elements in various embodiments of the present disclosure, the elements are not limited to these terms. These terms are used only to tell one element from another element. An embodiment described and exemplified herein includes a complementary embodiment thereof.

The terms used in the specification are for the purpose of describing particular embodiments only and are not intended to be limiting of the present disclosure. As used in the specification, the singular forms "a", "an" and "the" are intended to include the plural forms as well, unless the context clearly indicates otherwise. It will be further understood that the terms "comprises" and/or "comprising", when used in the specification, specify the presence of stated features, integers, steps, operations, elements, and/or components, but do not preclude the presence or addition of one or more other features, integers, steps, operations, elements, components, and/or groups thereof.

Hereinafter, embodiments of the present disclosure will now be described more fully with reference to accompanying drawings.

FIG. 1 is a conceptual diagram of a strain measuring device according to an example embodiment of the present disclosure.

Figure 2:
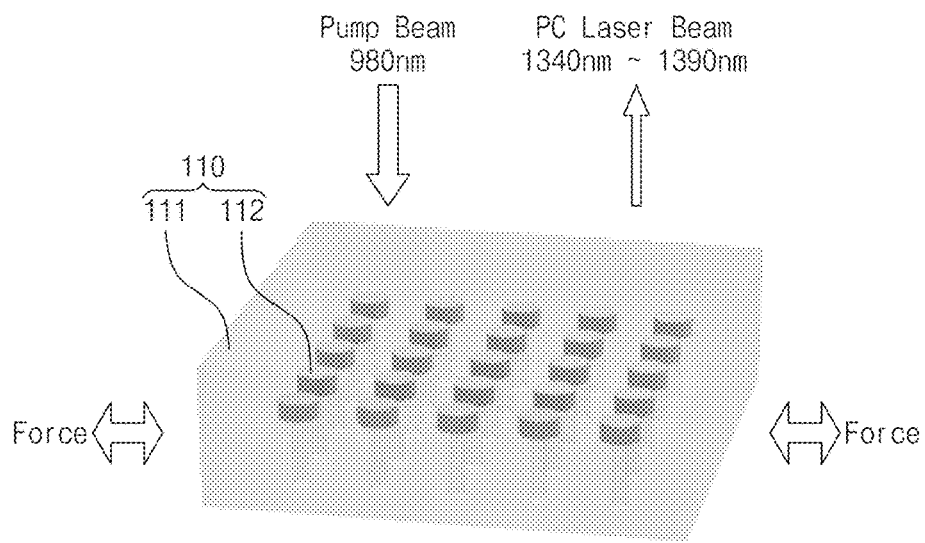
FIG. 2 is a perspective view of a photonic crystal laser in FIG. 1.

FIG. 2 is a perspective view of a photonic crystal laser in FIG. 1.

Figure 3:
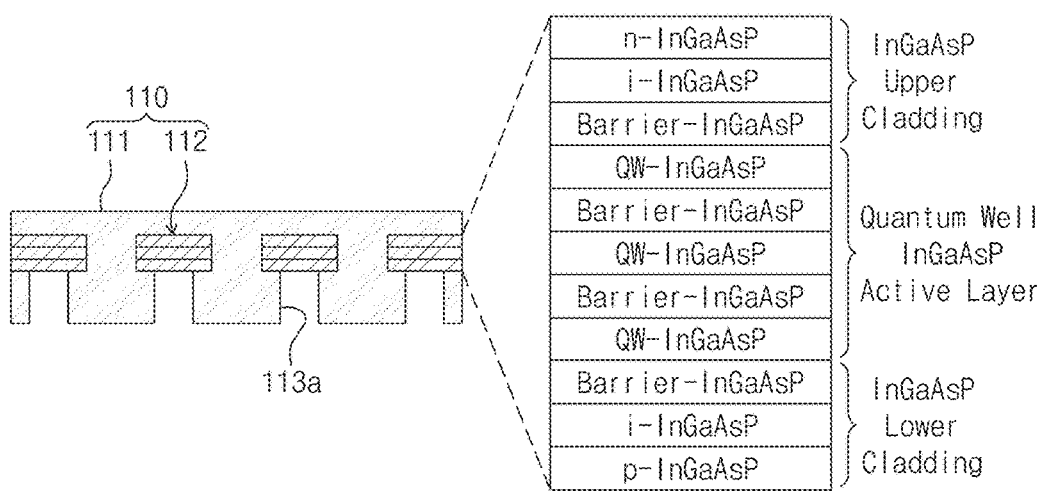
FIG. 3 is a cross-sectional view of the photonic crystal laser in FIG. 2.

FIG. 3 is a cross-sectional view of the photonic crystal laser in FIG. 2.

Referring to FIGS. 1 through 3, a strain measuring device 100 includes a photonic crystal laser 110 buried in a flexible substrate 111, a pump beam source 140 configured to provide a pump beam to the photonic crystal laser 110, a wavelength detector 150 configured to detect a laser wavelength varying depending on an external pressure applied to the photonic crystal laser 110, and a processor 160 configured to calculate the degree of transformation of the photonic crystal laser using the laser wavelength.

The photonic crystal laser 110 includes a flexible substrate 111 and a photonic crystal structure 112 buried in the flexible substrate 111. The photonic crystal laser 110 may receive a pump beam to emit a laser beam having a wavelength depending on a structure of a resonator determined by the photonic crystal structure 112. The photonic crystal laser 110 may be attached to a measurement target 102 in the form of a film. When the measurement target 102 is transformed, a wavelength of the photonic crystal laser 110 may vary depending on the degree of the transformation. The photonic crystal laser 110 will be described in detail later. The measurement target 102 may be changed into pressure applying means for varying the wavelength of the photonic crystal laser 110.

The pump beam source 140 may provide a pump beam to the photonic crystal laser 110. The pump beam source 140 may be a pulse laser. The pump beam source 140 may be a diode laser of 980 nm. The pump beam source 140 may be suitably selected according to a gain material of the photonic crystal laser 110. The pump beam source 140 is used to oscillate the photonic crystal laser. An output of the pump beam may be greater than or equal to 600 microwatts (μW). The output of the pump beam may output threshold power (less than 600 μW) or above to oscillate the photonic crystal laser 110.

The wavelength detector 150 may detect a center wavelength of the photonic crystal laser 110. For example, the wavelength detector 150 may be a spectrometer.

The processor 160 may convert variation of a center wavelength and a wavelength of a laser detected by the wavelength detector 150 into the degree of transformation of the photonic crystal laser 110. The processor 160 may include a display unit configured to display the degree of transformation of the photonic crystal laser 110.

A dichromatic mirror 130 may receive and transfer the emitted pump beam of the pump beam source 140 to the photonic crystal laser 110, and may receive and transfer a laser beam emitted from the photonic crystal laser 110 to the wavelength detector 150. The dichromatic mirror 130 may reflect a pump beam of 980 nm and may transmit a laser beam having a band of 1400 nm of the photonic crystal laser 110.

A parallel beam lens 173 may be disposed between the pump beam source 140 and the dichromatic mirror 130 to convert the pump beam into a parallel beam. Thus, the parallel beam may be reflected by the dichromatic mirror 130 to be transferred to the photonic crystal laser 110.

An object lens 120 may be disposed between the dichromatic mirror 130 and the photonic crystal laser 110 to focus the pump beam onto the photonic crystal laser 110. The object lens 120 may operate an object of a microscope or may focus and provide the pump beam to a specific position of the photonic crystal laser 110.

An illumination beam source 171 may be used to check a surface shape of the photonic crystal laser 110. The illumination beam source 171 may be a white light source of an infrared area or a visible ray area.

A beam coupler 172 may be disposed between the dichromatic mirror 130 and the object lens 120 to receive and provide an illumination beam to the photonic crystal laser 110. The beam coupler 172 may reflect and provide the illumination beam to the photonic crystal laser 110. Thus, the illumination beam reflected on the photonic crystal laser 110 may be provided to the camera 177 after transmitting the beam coupler 172 and the dichromatic mirror 130. As a result, the camera 177 may display a surface shape or transformation of the photonic crystal laser 110 as a specific pattern.

A reflection mirror 174 may be disposed between the dichromatic mirror 130 and the wavelength detector 150 to change a beam path. A splitter 176 may be disposed between the reflection mirror 174 and the wavelength detector 150 to split a beam. The camera 177 may pick up an image using a beam split from the beam splitter 176.

A silicon block 175 may prevent the pump beam of 980 nm from entering the camera 175 or the wavelength detector 150.

The photonic crystal laser 110 may include a disk-shaped photonic crystal structure 112 two-dimensionally disposed in a matrix on a disposition plane and a flexible substrate 111 disposed to support the photonic crystal structure 112 and to cover at least a side surface of the photonic crystal structure. The photonic crystal laser 110 may provide an oscillation to the same pump beam at different wavelengths according to the degree of flexibility or transformation. Thus, the photonic crystal laser 110 may operate as a strain sensor.

An arrangement period of the photonic crystal structure 112 may be between 550 and 700 nm. A laser gain medium of the photonic crystal structure 112 may be InGaAsP spontaneously emitted at an infrared area or AlGaAs spontaneously emitted around 650 nm.

The photonic crystal structure 112 may include an InGaAsP lower cladding layer, a quantum well InGaAsP active layer, and an InGaAsP upper cladding layer that are sequentially stacked. The InGaAsP lower cladding layer may include a P-type InGaAsP layer, an intrinsic InGaAsP layer, and a barrier InGaAsP layer. The quantum well InGaAsP active layer may include a quantum well InGaAsP layer layer/a barrier InGaAsP layer/a quantum well InGaAsP layer/a barrier InGaAsP layer/a quantum well InGaAsP layer. The InGaAsP upper cladding layer may include a barrier InGaAsP layer/an intrinsic InGaAsP layer/ an N-type InGaAsP layer.

The photonic crystal structure 112 may include disks two-dimensionally arranged in a square lattice. The disks may have at least 10 by 10 array. Preferably, the disks may have at least 20 by 20 array. A radius of the disk may be about 200 nm and a thickness thereof may be about 250 nm.

The flexible substrate 111 may include at least one of polydimethylsiloxane (PDMS), polyimide or polyethylene terephthalate (PET). The flexible substrate 111 may cover a side surface and a top surface of the disk-shaped photonic crystal structure 112. The flexible substrate 111 may include a through-hole 113a formed at a lower portion of the disk-shaped photonic crystal structure 112. A diameter of the through-hole 113a may be smaller than that of the disk-shaped photonic crystal structure 112. The through-hole 113a may be formed by selectively etching a photonic crystal support 113b. The photonic crystal support 113b may be made of InP.

According to a modified embodiment of the present disclosure, the through-hole 113a may be filled with the same material as the flexible substrate 111.

As a factor to determine a laser wavelength of the photonic crystal structure 112, a photonic crystal structural parameter is most important. A period of a square lattice photonic crystal array is 650 nm, a disk of the photonic crystal structure 112 is InGaAsP having a three-layered quantum well, and the disk has a diameter of 200 nm and a thickness of 250 nm. A radius of the photonic crystal support 113b is 120 nm and a height thereof is 800 nm. When the photonic crystal support 113b is InP, a refractive index (about 3.3) of the photonic crystal support 113b and a refractive index (about 1.4) of the flexible substrate of the PDMS are factors to determine the wavelength of the photonic crystal laser 110.

According to an example embodiment of the present disclosure, the structural parameter is determined to make laser oscillation possible at an infrared wavelength with respect to refractive indices of InGaAsP and PDMS.

According to an example embodiment of the present invention, a photonic crystal laser is provided using InGaAsP, which is a material spontaneously emitted at an infrared area (1300 to 1500 nm), as a gain material. A resonator resonating at a longer infrared wavelength than visible ray has a larger size than a resonator of a visible ray area and thus is easily fabricated. This is because a size of a resonator is generally proportional to a length of a wavelength.

A photonic crystal laser corresponding to another area (e.g., the visible ray area) may be fabricated to be used as a strain gauge. AlGaAs is a material spontaneously emitted at red color (about 650 nm). If a photonic crystal structure of a nail-like array structure in which AlGaAs is a nail head (a disk of the photonic crystal structure) is formed to have a resonance mode around 650 nm, a strain gauge operating in the visible ray area may be provided.

Hereinafter, a method for fabricating a photonic crystal laser according to an example embodiment of the present disclosure will now be described below.

Figure 4:
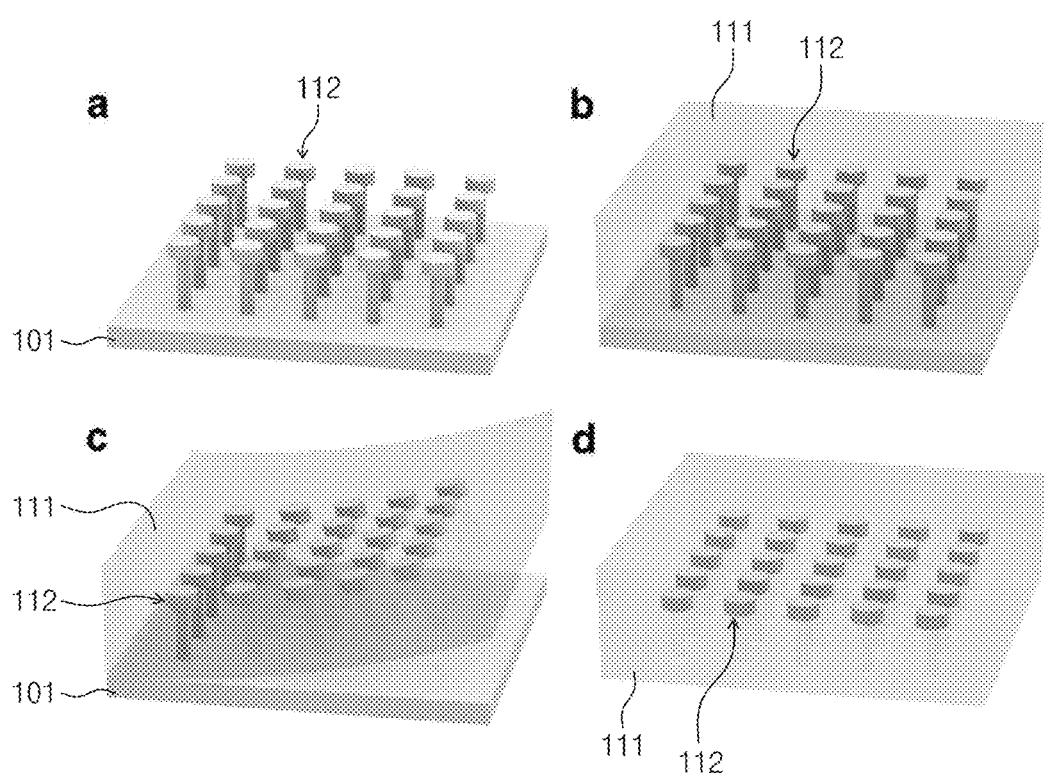
FIG. 4 is a perspective view illustrating a method for fabricating a photonic crystal laser according to an example embodiment of the present disclosure.

FIG. 4 is a perspective view illustrating a method for fabricating a photonic crystal laser according to an example embodiment of the present disclosure.

Referring to FIG. 4, according to the method, a photonic crystal structure of a steel nail structure is formed on a substrate 101 (a). Then, polymer is coated on the substrate 101 (b). And then, the substrate 101 is physically isolated (c) to form a photonic crystal laser buried in the polymer (d). The polymer operates as a flexible substrate.

Figure 5:
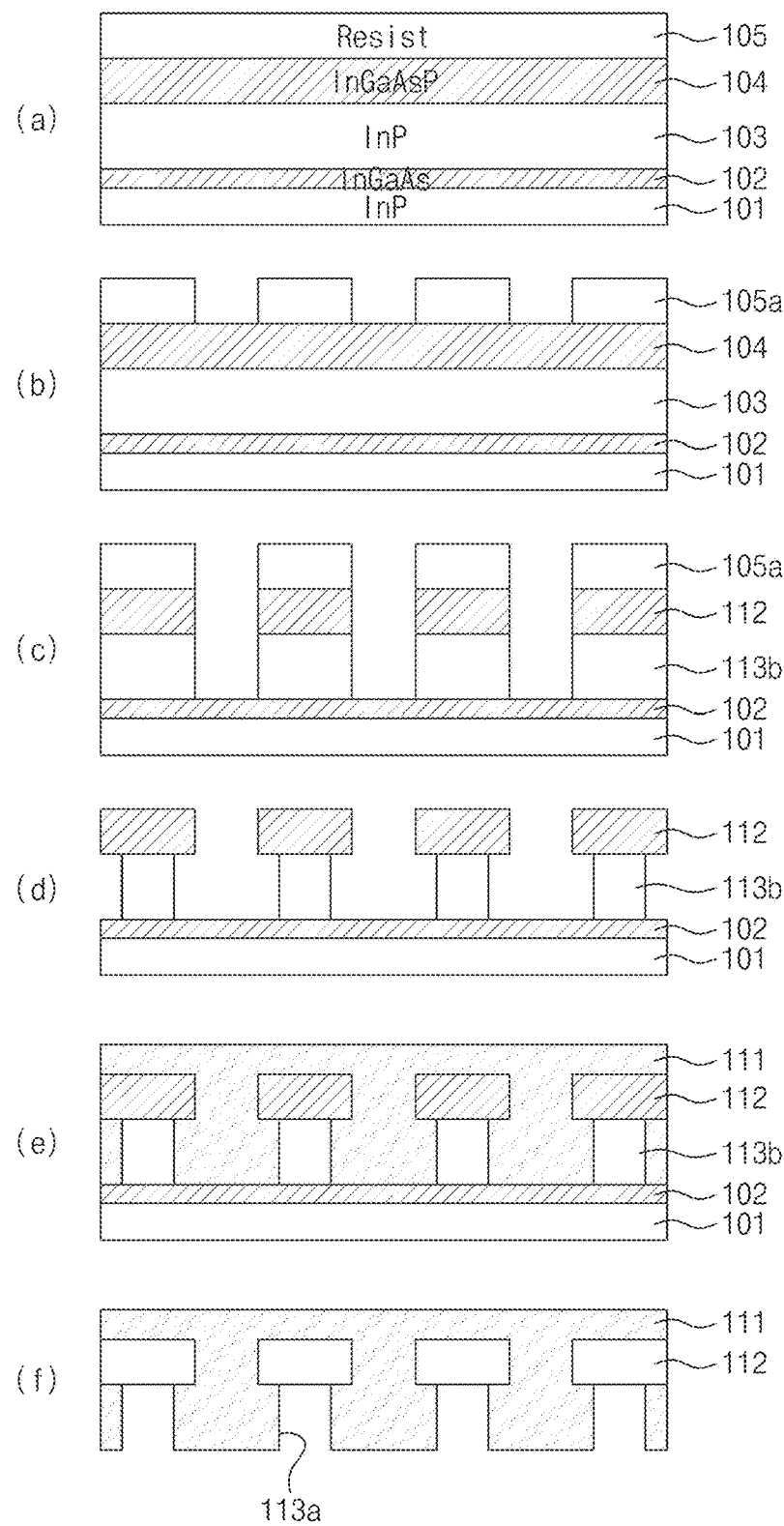
FIG. 5 includes cross-sectional views illustrating a method for fabricating a photonic crystal laser according to an example embodiment of the present disclosure.

FIG. 5 includes cross-sectional views illustrating a method for fabricating a photonic crystal laser according to an example embodiment of the present disclosure.

Referring to FIG. 5, the method for fabricating a photonic crystal laser includes forming an etch-stop layer 102 on a substrate 101, forming a buffer layer on the etch-stop layer 102, forming a photonic crystal active layer 104 on the buffer layer 103, coating a resist 105 on the photonic crystal active layer 104 and patterning the coated resist 105 to form a resist mask 105a, dry-etching the photonic crystal active layer 104 and the buffer layer 103 using the resist mask 105a as an etch mask to form a two-dimensionally disposed photonic crystal structure 112, selectively wet-etching the buffer layer 103 of the photonic crystal structure 112 to form a thinned photonic crystal support 113b, coating and curing a polymer 111 on the substrate 101 where the thinned photonic crystal support 113b is formed, removing the substrate 101 to provide the photonic crystal structure 112 buried in the polymer 111, and removing the thinned photonic crystal support 113b through wet etching.

Referring to FIG. 5(a), an etch-stop layer 102 is formed on a substrate 101. A buffer layer 103 is formed on the etch-stop layer 102. A photonic crystal active layer 104 is formed on the buffer layer 103. A resist 105 is coated on the photonic crystal active layer 104 and then is patterned to form a resist mask 105a. The substrate 101 may be InP, the etch-stop layer 102 may be InGaAs, the buffer layer 103 may be InP, and the photonic crystal active layer 104 may include InGaAsP. The photonic crystal active layer 104 may include an InGaAsP lower cladding layer, a quantum well InGaAsP active layer, and an InGaAsP upper cladding layer that are sequentially stacked. The InGaAsP lower cladding layer may include a P-type InGaAsP layer, an intrinsic InGaAsP layer, and a barrier InGaAsP layer. The quantum well InGaAsP active layer may include a quantum well InGaAsP layer/a barrier InGaAsP layer/a quantum well InGaAsP layer/a barrier InGaAsP layer/a quantum well InGaAsP layer. The InGaAsP upper cladding layer may include a barrier InGaAsP layer/an intrinsic InGaAsP layer/an N-type InGaAsP layer.

The resist mask 105a may be formed by an electron beam lithography process, a photolithography process or the like.

Referring to FIG. 5(b) and FIG. 5(c), the photonic crystal active layer 104 and the buffer layer 103 are dry-etched using the resist mask 105a as an etch mask to form a two-dimensionally disposed photonic crystal structure 112. The dry etching may be chemically assisted ion beam etching performed by accelerating argon ions under a chlorine gas atmosphere. A cylindrical array structure may be formed by the dry etching. After the dry etching is completed, the resist mask may be removed using oxygen ($O_2$) plasma.

Referring to FIG. 5(d), the buffer layer 103 of the photonic crystal structure 112 is selectively wet-etched to form a thinned photonic crystal support 113b. In the wet etching, the photonic crystal support 113b made of InP is thinned using an HCl solution to form a nail-like array structure. The wet etching may employ a selective wet etching process in which InP is dissolved in hydrochloric acid while InGaAsP is not dissolved in the hydrochloric acid.

According to a modified embodiment of the present disclosure, the photonic crystal laser 112 may oscillate although there is a photonic crystal support (or InP post). However, if there is no photonic support (or InP post), a quality factor of a resonator that is an important factor of a laser may be improved. Thus, the photonic crystal laser 112 may be drive with less energy of pumping beam.

Referring to FIG. 5(e), a polymer 111 is coated and cured on the substrate 101 where the thinned photonic crystal support 113b is formed. The polymer 111 may be polydimethylsiloxane (PDMS). The coating of the polymer 111 may be carried out using spin coating or a roller. The polymer 111 may be thermally cured or UV-cured.

Referring to FIG. 5(f), the substrate 101 is removed to provide the photonic crystal structure 112 buried in the polymer 111. The substrate 101 and the polymer 111 are physically separated by external force. The thinned photonic crystal support 113b is removed by wet etching. The wet etching may be performed using the HCl solution. Thus, the photonic crystal laser is fabricated. The photonic crystal laser may include a flexible substrate in which a photonic crystal structure is buried.

The polymer 111 may include at least one of polydimethylsiloxane (PDMS), polyimide or polyethylene terephthalate (PET).

Figure 6:
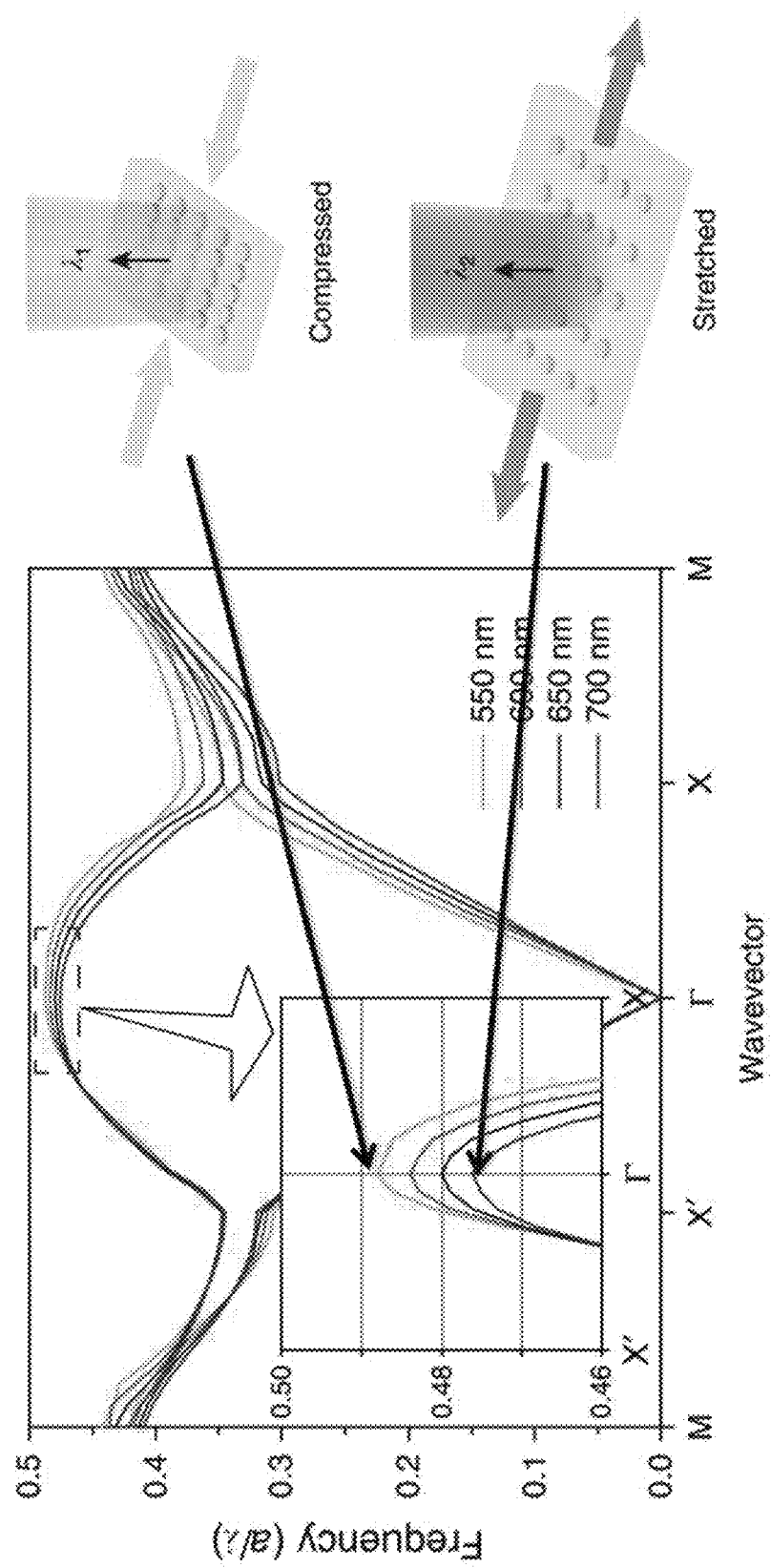
FIG. 6 shows a result obtained by checking a band structure for a photonic crystal structure according to an example embodiment of the present disclosure.

FIG. 6 shows a result obtained by checking a band structure for a photonic crystal structure according to an example embodiment of the present disclosure.

Referring to FIG. 6, a squared portion indicates a Γ-point band-edge mode of a laser described in the present disclosure. In the Γ-point band-edge mode, a resonance wavelength is determined according to a lattice constant of a nail head structure. As the lattice constant increases from 550 nm to 700 nm, a resonant frequency decreases.

Based on the above principle, when the structure is transformed by applying a pressure to a photonic crystal laser according to an example embodiment of the present disclosure, the photonic crystal laser may be used as a sensor to measure a strain by checking variation of an excited laser wavelength.

Figure 7:
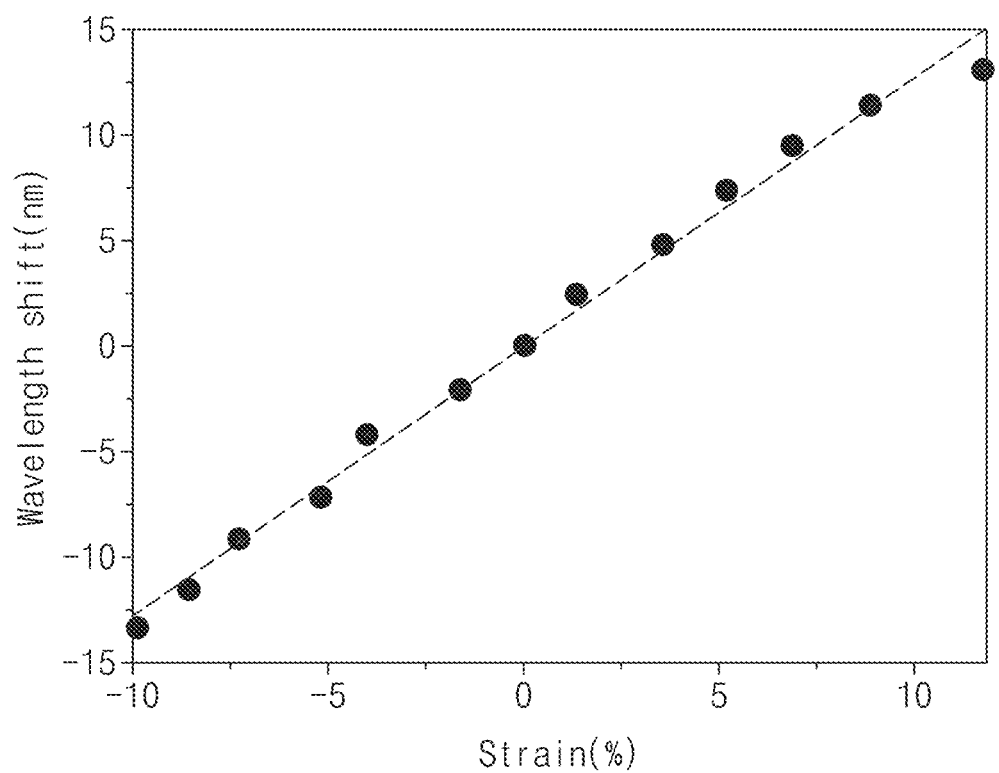
FIG. 7 shows a test result indicating wave shift according to a strain applied from a photonic crystal laser according to an example embodiment of the present disclosure.

FIG. 7 shows a test result indicating wave shift according to a strain applied from a photonic crystal laser according to an example embodiment of the present disclosure.

FIG. 7 shows a test result indicating wave shift according to a strain applied from a photonic crystal laser according to an example embodiment of the present disclosure.

Referring to FIG. 7, a wavelength shift is given by a difference between a wavelength when an external force is not applied and a wavelength when the external force is applied. The photonic crystal laser 110 has a very narrow wavelength linewidth of 0.6 nm or less when a pressure is applied. Thus, the photonic crystal laser 110 may sense a strain very sensitively. Additionally, the photonic crystal laser 110 maintains the narrow linewidth irrespective of variation of the strain. A positive value of the strain means stretching, and a negative value thereof means compression. Additionally, the photonic crystal laser 110 maintains the narrow linewidth irrespective of variation of the strain. The wavelength shift is changed linearly with respect to the strain and thus separate signal processing is not required. A positive value of the strain means stretching, and a negative value thereof means compression. The wavelength shift is 26 nm with respect to the strain change from −10 percent to 12 percent.

Figure 8:
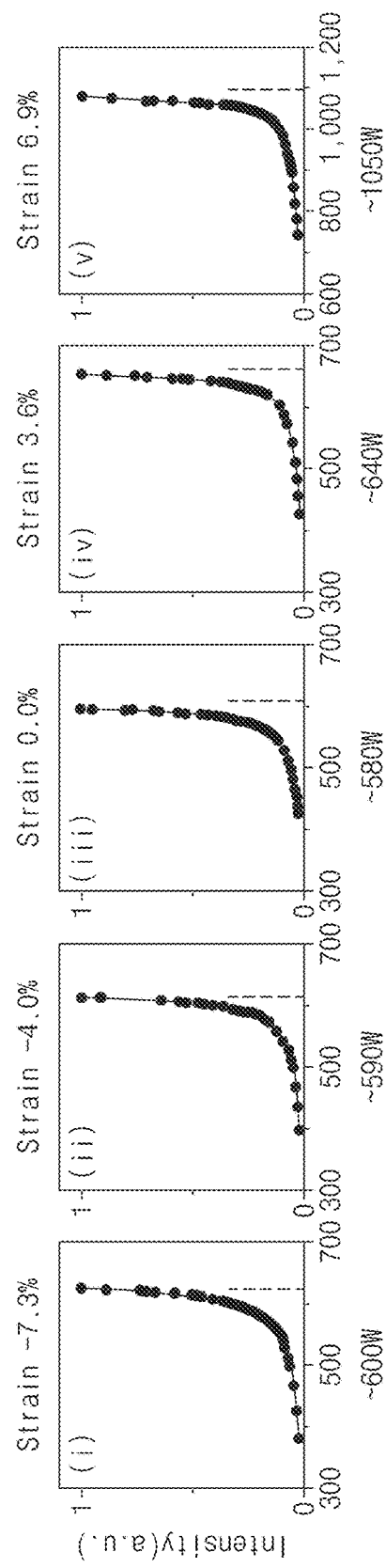
FIG. 8 shows a threshold test result of a pumping beam to oscillate a laser in a photonic crystal laser according to an example embodiment of the present disclosure.

FIG. 8 shows a threshold test result of a pumping beam to oscillate a laser in a photonic crystal laser according to an example embodiment of the present disclosure.

Referring to FIG. 8, a pump laser beam having power of a threshold value or greater is required to oscillate the photonic crystal laser 110. A threshold value of pump laser beam ranging from −7.3 to 6.9 percent at each strain was checked. The threshold value means minimum power of a pump beam source required to oscillate a laser. The photonic crystal laser 110 exhibited a threshold value of about 600 mW in most strain area and may sufficiently operate as a laser for a pump beam source of about 1000 mW or greater.

Figure 9:
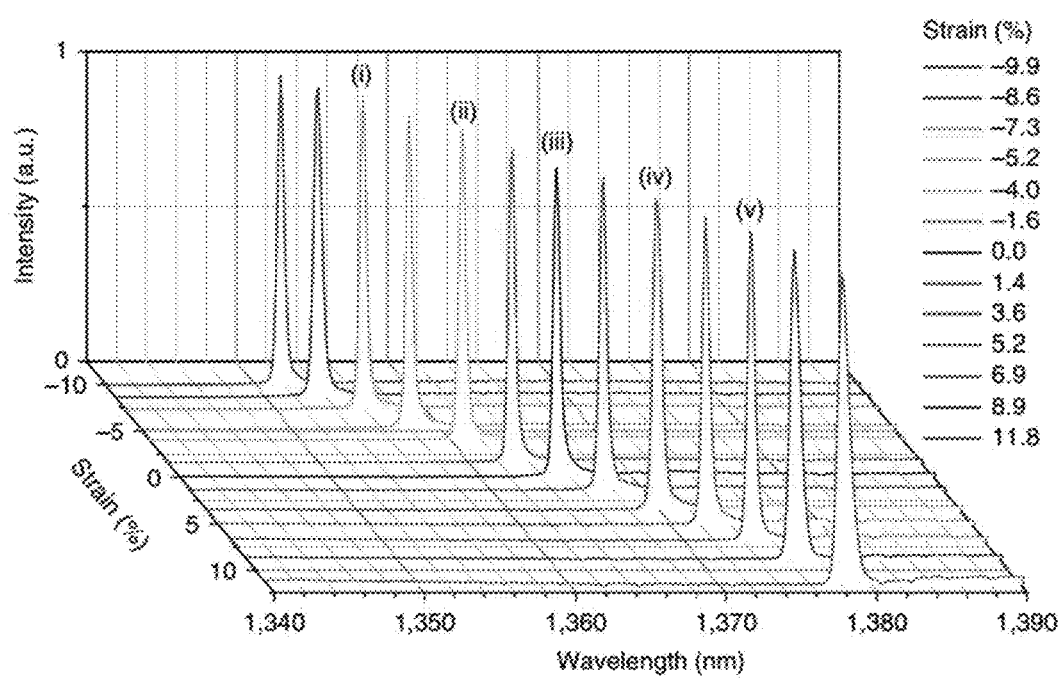
FIG. 9 shows a strain-dependent spectrum of a photonic crystal laser according to an example embodiment of the present disclosure.

FIG. 9 shows a strain-dependent spectrum of a photonic crystal laser according to an example embodiment of the present disclosure.

Referring to FIG. 9, a center wavelength of the photonic crystal laser 110 corresponds to 1350 to 1380 nm with respect to a strain of −10 to +12 percent. The pump beam source is a laser diode of 980 m that operates in a pulse mode.

Figure 10:
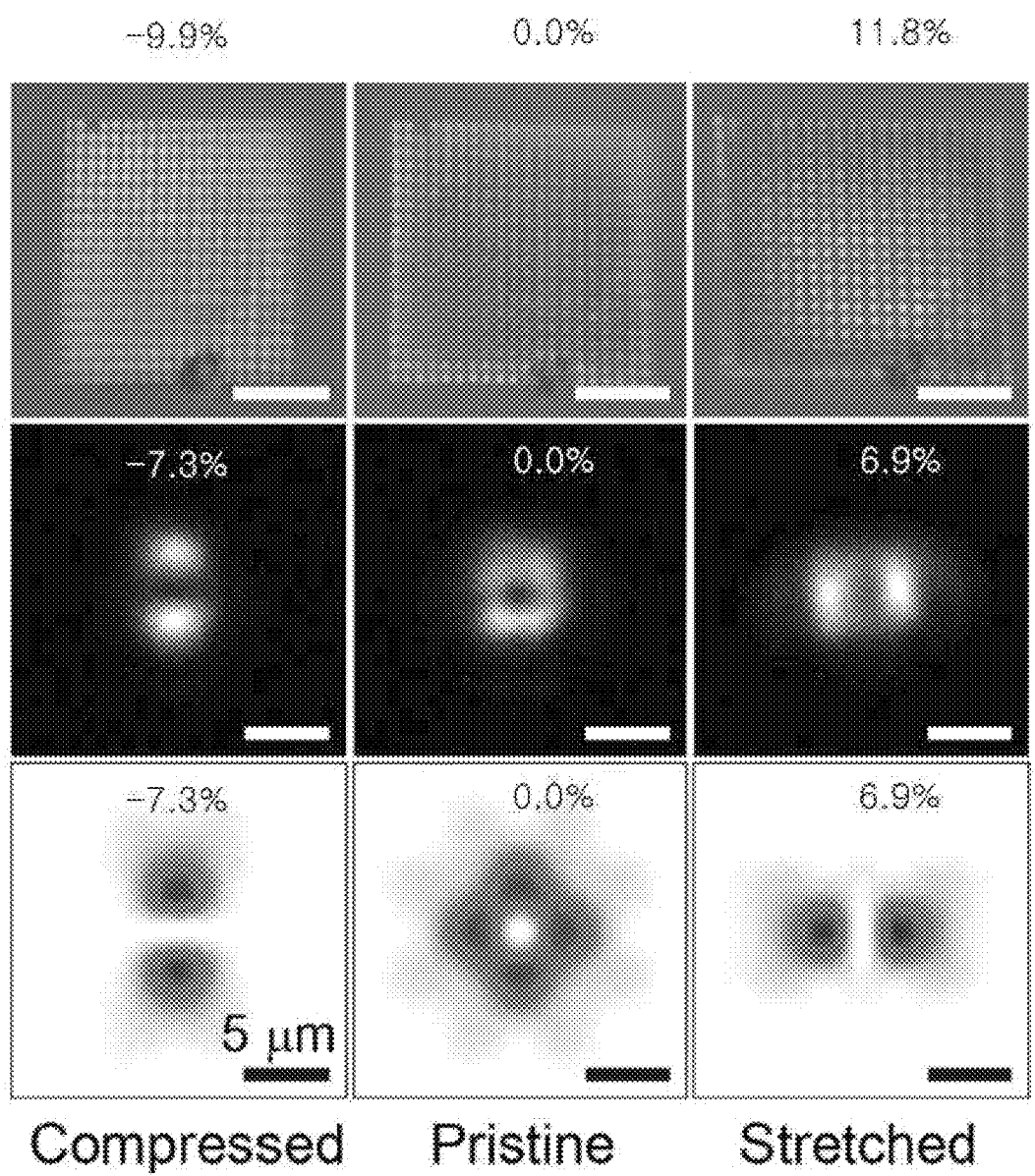
FIG. 10 shows an optical micrograph, a photograph of oscillation mode, and a simulation result of the oscillation mode, depending on a strain, of a photonic crystal laser according to an example embodiment of the present disclosure.

FIG. 10 shows an optical micrograph, a photograph of oscillation mode, and a simulation result of the oscillation mode, depending on a strain, of a photonic crystal laser according to an example embodiment of the present disclosure.

Referring to FIG. 10, an optical micrograph of a photonic crystal laser was obtained using a color camera of a visible ray area, which is mounted on a microscope, under an illumination light without a pump beam. An image of the oscillation mode is picked up via a camera 177. A shape (direction) of the strain may be understood through the image of the camera 177. The approximate degree of the strain may be checked through the image of the camera 177. When a compression force is applied under the illumination light, a green color is shown. When a stretching force is applied under the illumination light, a yellow color is shown.

In the case of the oscillation mode, two dots are vertically separated from each other when the compression force is applied and are horizontally separated from each other when the stretching force is applied. This result matches the simulation result.

Figure 11:
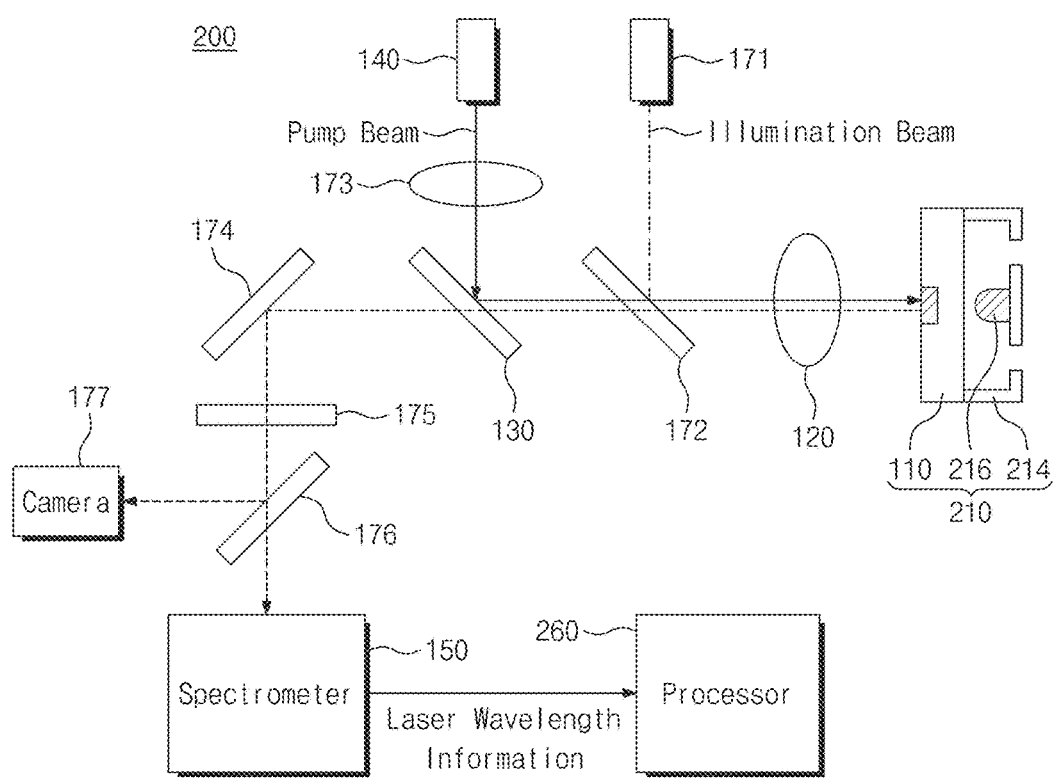
FIG. 11 is a conceptual diagram of a pH sensor based on a photonic crystal laser according to an example embodiment of the present disclosure.

FIG. 11 is a conceptual diagram of a pH sensor based on a photonic crystal laser according to an example embodiment of the present disclosure.

Referring to FIG. 11, a pH measuring device 200 includes a pH sensor 210 based on a photonic crystal laser 110, a pump beam source 140 configured to provide a pump beam to the photonic crystal laser 110, a wavelength detector configured to detect a laser wavelength varying depending on an external pressure applied to the photonic crystal laser 110, and a processor 260 configured to calculate the transformation degree of the photonic crystal laser 110 using the laser wavelength.

The pH sensor 210 based on the photonic crystal laser 110 includes a housing 214 having a cavity formed therein and including an inlet channel and an outlet channel, a pH-sensitive hydrogel 216 disposed inside the housing 214, and a photonic crystal laser 110 disposed on one surface of the pH-sensitive hydrogel 216. The pH-sensitive hydrogel 216 provides a volume variation depending on a pH level of a liquid solution, and the photonic crystal laser 110 is transformed by the volume variation.

The housing 214 may be made of a transparent material and may maintain a fixed volume. The material of the housing 214 may be a transparent glass material or a transparent plastic-based material with little volume expansion. The housing 214 may include an inlet through which a liquid flows in and an outlet through which the liquid flows out. The photonic crystal laser 110 may be a cover of the housing 214. Thus, the housing 214 and the photonic crystal laser 110 may provide cavities therein.

The pH-sensitive hydrogel 216 is a material whose volume varies depending on a pH level of a surrounding material. The pH-sensitive hydrogel 216 may include functional groups such as —COOH, —SO3H or —NH2.

The photonic crystal laser 110 includes a disk-shaped photonic crystal structure 112 two-dimensionally disposed in a matrix on a disposition plane and a flexible substrate 111 disposed to support the photonic crystal structure 112 and to cover at least a side surface of the photonic crystal structure 112.

An aqueous solution having a given pH level is injected into the inlet of the housing 214, the liquid solution comes in contact with the pH-sensitive hydrogel, and the pH-sensitive hydrogel performs volume expansion.

According to the pH level of the aqueous solution, different mechanical strains are applied to the pH sensor 210 based on the photonic crystal laser 110. Thus, the pH sensor 210 based on the photonic crystal laser 110 provides a laser wavelength depending on the pH level.

Figure 12:
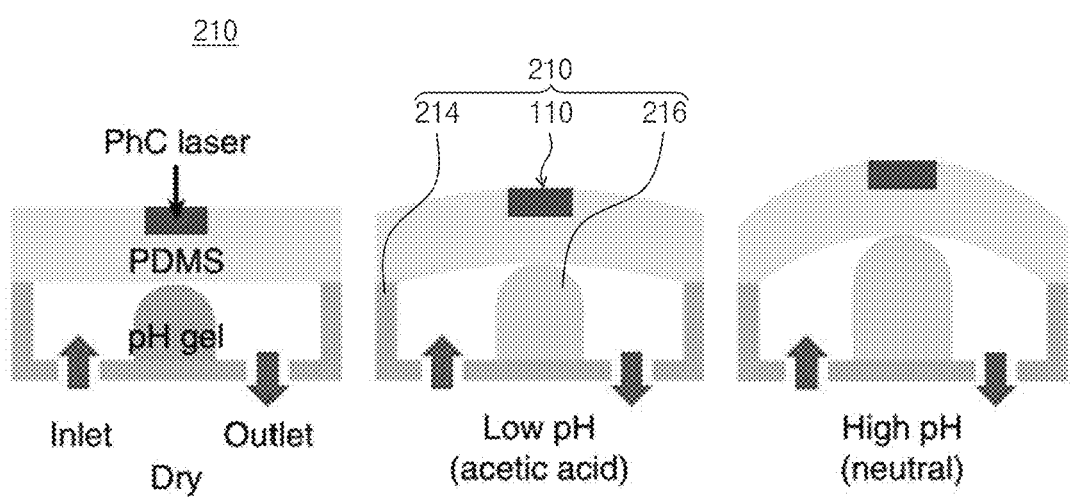
FIG. 12 is a conceptual diagram illustrating pH-dependent volume expansion according to another example embodiment of the present disclosure.

FIG. 12 is a conceptual diagram illustrating pH-dependent volume expansion according to another example embodiment of the present disclosure.

Referring to FIG. 12, when the housing 214 is in a dry state without an aqueous solution, the pH-sensitive hydrogel 216 may maintain its original volume. When pH of the aqueous solution is low (acetic acid; pH=2.5), the pH-sensitive hydrogel 216 may be slightly expanded. When the pH of the aqueous solution is neutral (pH=7), the pH-sensitive hydrogel 216 may be significantly expanded. The expansion degree of the pH-sensitive hydrogel 216 depending on the aqueous solution may provide a bending degree of the photonic crystal laser 212. According to the bending (transformation) degree, the photonic crystal laser 212 may oscillate at a different wavelength.

Figure 13:
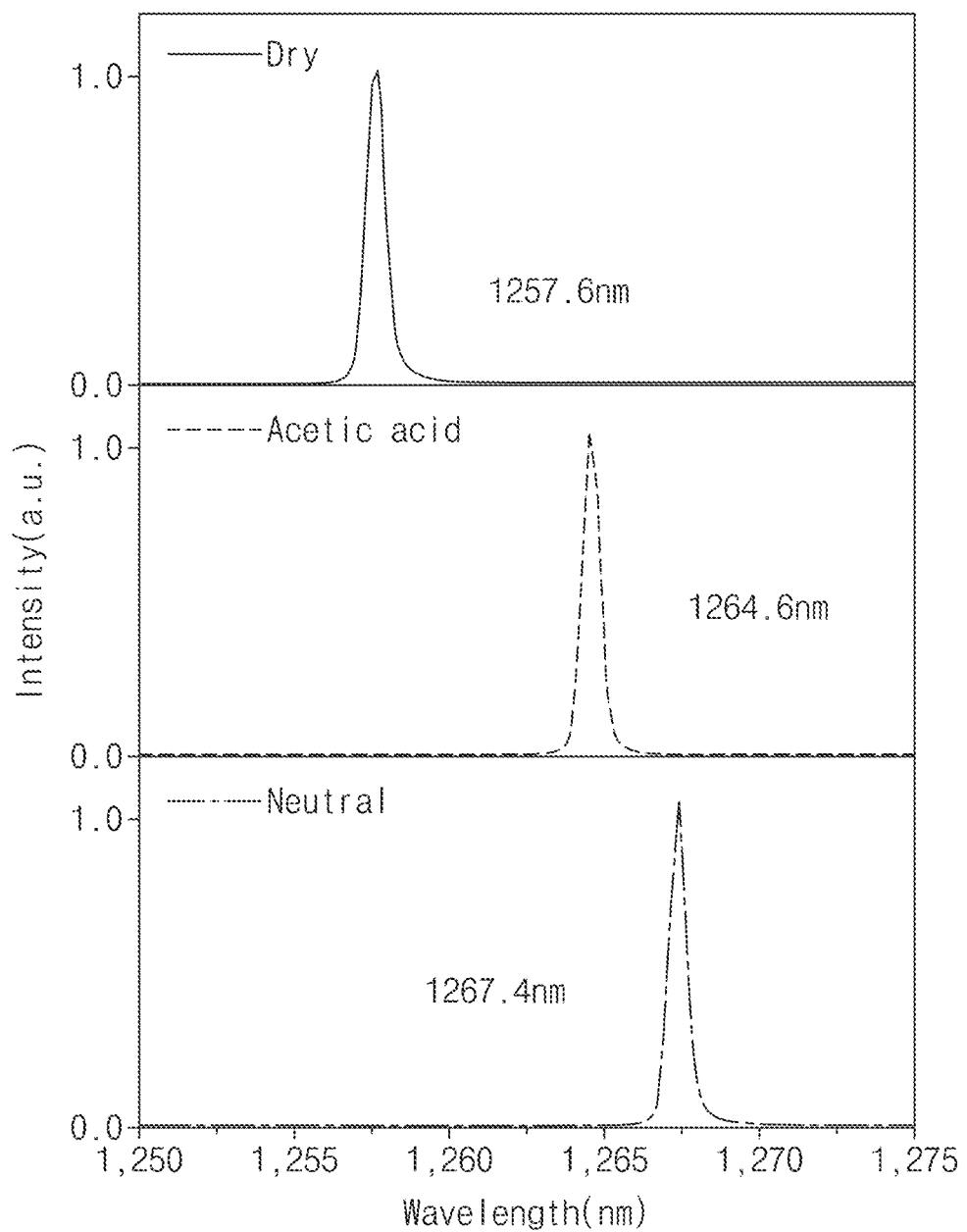
FIG. 13 shows a result of lasing wavelength, depending on pH level of an aqueous solution, of a photonic crystal laser according to an example embodiment of the present disclosure.

FIG. 13 shows a result of lasing wavelength, depending on pH level of an aqueous solution, of a photonic crystal laser according to an example embodiment of the present disclosure.

Referring to FIG. 13, a wavelength of laser is 1257.6 nm in a dry state, 1264.6 nm in an acetic acid state, and 1267.4 nm in a neutral state.

A photonic crystal laser according to an example embodiment of the present disclosure may be widely used in various fields of application such as a building structural change measuring sensor, a wearable device having a motion sensor function, and a micro biosensor for sensing a chemical reaction.

According to example embodiments of the present disclosure, a novel strain gauge or strain sensor having a wide measuring range and a high resolution may be fabricated using a photonic crystal laser having optically excellent characteristics. In particular, a frequency of the photonic crystal laser is most stable physical quality that is hardly affected by an external environment and may provide high accuracy and stability when transformation of an object is manifested as a frequency. These features may be implemented through a photic crystal resonator.

Although the present disclosure and its advantages have been described in detail, it should be understood that various changes, substitutions and alterations can be made herein without departing from the spirit and scope of the disclosure as defined by the following claims.

What is claimed is:

1. A method for fabricating a photonic crystal laser, comprising:
   forming an etch-stop layer on a substrate;
   forming a buffer layer on the etch-stop layer;
   forming a photonic crystal active layer on the buffer layer;
   coating a resist on the photonic crystal active layer and patterning the coated resist to form a resist mask;
   dry-etching the photonic crystal active layer and the buffer layer using the resist mask as an etch mask to form a two-dimensionally disposed photonic crystal structure;
   selectively wet-etching the buffer layer of the two-dimensionally disposed photonic crystal structure to form a thinned photonic crystal support;
   coating and curing a polymer on the substrate where the thinned photonic crystal support is formed;
   removing the substrate to provide the two-dimensionally disposed photonic crystal structure buried in the polymer; and
   removing the thinned photonic crystal support through wet etching;

wherein the two-dimensionally disposed photonic crystal structure is two-dimensionally disposed in a matrix on a disposition plane without defects;
wherein the photonic crystal laser comprises:
a flexible substrate disposed to support the two-dimensionally disposed photonic crystal structure and to cover at least a side surface of the two-dimensionally disposed photonic crystal structure;
wherein the flexible substrate comprises a through-hole formed at a lower portion of the two-dimensionally disposed photonic crystal structure and a diameter of the through-hole is smaller than a diameter of the two-dimensionally disposed photonic crystal structure;
wherein the two-dimensionally disposed photonic crystal structure oscillates in a Γ-point band-edge mode;
wherein the photonic crystal laser is attached to a measurement target;
wherein an arrangement period of the two-dimensionally disposed photonic crystal structure is between 550 and 700 nm;
wherein a laser gain medium of the two-dimensionally disposed photonic crystal structure is InGaAsP spontaneously emitted at an infrared region from 1350 nm to 1380 nm;
wherein the two-dimensionally disposed photonic crystal structure includes an InGaAsP lower cladding layer, a quantum well InGaAsP active layer, and an InGaAsP upper cladding layer that are sequentially stacked;
wherein the through-hole is an empty space; and
wherein the through-hole is formed by selectively etching a photonic crystal support.

2. The method as set forth in claim 1, wherein the substrate is InP,
the etch-stop layer is InGaAs,
the buffer layer is InP, and
the photonic crystal active layer includes InGaAsP.

3. The method as set forth in claim 1, wherein the polymer includes at least one of polydimethylsiloxane (PDMS), polyimide or polyethylene terephthalate (PET).

4. The method as set forth in claim 1, wherein the dry etching is chemically assisted ion beam etching performed by accelerating argon ions under a chlorine gas atmosphere.

5. A strain measuring device comprising:
a photonic crystal laser buried in a flexible substrate;
a pump beam source configured to provide a pump beam to the photonic crystal laser and to oscillate the photonic crystal laser;
a wavelength detector configured to detect a laser wavelength varying depending on an external pressure applied to the photonic crystal laser; and
a processor configured to calculate the degree of transformation of the photonic crystal laser using the laser wavelength,
wherein the photonic crystal laser comprises:
a disk-shaped photonic crystal structure two-dimensionally disposed in a matrix on a disposition plane without defects; and
a flexible substrate disposed to support the photonic crystal structure and to cover at least a side surface of the photonic crystal structure,
wherein the flexible substrate comprises a through-hole formed at a lower portion of the disk-shaped photonic crystal structure and a diameter of the through-hole is smaller than a diameter of the disk-shaped photonic crystal structure,
wherein the photonic crystal structure oscillates in a Γ-point band-edge mode,
wherein the photonic crystal laser is attached to a measurement target,
wherein an arrangement period of the photonic crystal structure is between 550 and 700 nm,
wherein a laser gain medium of the photonic crystal structure is InGaAsP spontaneously emitted at an infrared region from 1350 nm to 1380 nm,
wherein the photonic crystal structure includes an InGaAsP lower cladding layer, a quantum well InGaAsP active layer, and an InGaAsP upper cladding layer that are sequentially stacked,
wherein the through-hole is an empty space,
wherein the through-hole is formed by selectively etching a photonic crystal support,
wherein the pump beam source has a power of a threshold value or greater to oscillate the photonic crystal laser, further comprising:
a dichromatic mirror configured to receive the pump beam emitted from the pump beam source and transmit a received pump beam to the photonic crystal laser and configured to receive a laser beam emitted from the photonic crystal laser and transmit a received laser beam to the wavelength detector;
a parallel beam lens disposed between the pump beam source and the dichromatic mirror; and
an object lens disposed between the dichromatic mirror and the photonic crystal laser to focus the pump beam onto the photonic crystal laser.

6. The strain measuring device as set forth in claim 5, further comprising at least one of:
an illumination light source configured to output an illumination light;
a beam coupler disposed between the dichromatic mirror and the object lens to receive and provide the illumination light to the photonic crystal laser;
a reflection mirror disposed between the dichromatic mirror and the spectrometer to change a beam path;
a beam splitter disposed between the reflection mirror and the spectrometer to split a beam; and
a camera configured to pick up an image using a beam split from the beam splitter.

7. The strain measuring device as set forth in claim 5, wherein the flexible substrate includes at least one of polydimethylsiloxane (PDMS), polyimide or polyethylene terephthalate (PET).

8. The strain measuring device as set forth in claim 5, wherein an output of the pump beam is greater than or equal to 600 microwatts.

* * * * *